(12) United States Patent
Takagi et al.

(10) Patent No.: US 7,238,169 B2
(45) Date of Patent: *Jul. 3, 2007

(54) SAFETY INDWELLING NEEDLE (75) Inventors: Nobuo Takagi, Osaka (JP); Masahisa Tanimoto, Osaka (JP); Yuki Hiraoka, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/065,578

(22) Filed: Feb. 25, 2005

(65) Prior Publication Data

US 2005/0192535 A1    Sep. 1, 2005

(30) Foreign Application Priority Data

Feb. 26, 2004   (JP)   ............................ 2004-051027

(51) Int. Cl.
*A61M 5/00*   (2006.01)
*A61M 5/32*   (2006.01)

(52) U.S. Cl. .................. 604/110; 604/192; 604/187
(58) Field of Classification Search ................ 604/110, 604/167.01, 187, 192, 197, 198, 263
See application file for complete search history.

(56) References Cited

U.S. PATENT DOCUMENTS

| | | | | |
|---|---|---|---|---|
| 5,419,766 A | * | 5/1995 | Chang et al. ................ | 604/110 |
| 5,447,501 A | * | 9/1995 | Karlsson et al. ............ | 604/198 |
| 5,743,891 A | | 4/1998 | Tolkoff et al. .............. | 604/282 |
| 5,830,190 A | | 11/1998 | Howell ........................ | 604/168 |
| 5,997,513 A | * | 12/1999 | Smith et al. ................. | 604/198 |
| 6,224,569 B1 | | 5/2001 | Brimhall ..................... | 604/164 |
| 6,352,520 B1 | | 3/2002 | Miyazaki ............... | 604/167.03 |
| 6,616,630 B1 | | 9/2003 | Woehr et al. ................ | 604/110 |
| 2002/0026154 A1 | * | 2/2002 | Chang ......................... | 604/198 |

FOREIGN PATENT DOCUMENTS

| | | |
|---|---|---|
| EP | 0 645 159 A1 | 9/1994 |
| EP | 0 750 918 A2 | 1/1997 |
| JP | 7-148270 A | 6/1995 |
| JP | 7-328116 A | 12/1995 |
| JP | 10-52499 A | 2/1998 |
| JP | 2002-102345 A | 4/2002 |
| WO | WO 03/011381 A1 | 2/2003 |
| WO | WO 03/082383 A1 | 10/2003 |
| WO | WO 2004/004819 A1 | 1/2004 |

* cited by examiner

*Primary Examiner*—Kevin C. Sirmons
*Assistant Examiner*—Benjamin Huh
(74) *Attorney, Agent, or Firm*—Kubovcik & Kubovcik (57) ABSTRACT A safety indwelling needle including an inner needle unit 1 having an inner needle 8, an inner needle hub 14 and a housing member 13 disposed at a distal side of the inner needle hub 14, and an outer needle unit 2 having an outer needle 4, an outer needle hub 5 and an outer needle cap 9, characterized in that the housing member 13 includes openings for allowing penetration of the inner needle 8 at a distal end and a proximal end thereof, an internal space for storing only a distal end portion of the inner needle 8 including a needlepoint 3 thereof when the inner needle 8 is drawn out from the outer needle 4, and a shielding member which automatically closes the opening at the proximal end of the housing member 13 by a magnetic force.

8 Claims, 13 Drawing Sheets

SAFETY INDWELLING NEEDLE

BACKGROUND OF THE INVENTION

The present invention relates to an indwelling needle assembly used for fluid infusion, hemodialysis or the like. More specifically, the invention relates to a safety indwelling needle provided with a safety mechanism.

In recent years, there has arisen a problem of a risk of transmission of AIDS or hepatitis virus to medical personnel due to accidental puncture by a pointed edge of an injection needle or the like which is contaminated by blood. Therefore, in an indwelling needle assembly including an inner needle and an outer needle, a safety indwelling needle in which the inner needle is covered after use without putting a cap again thereon to prevent accidental puncture has been invented.

For example, there is disclosed a safety indwelling needle in which an inner needle is retracted within a needle cover and stored therein by a spring when a button provided on the indwelling needle is pushed after use (for example, Japanese Patent Laid-Open No. 52499/1998).

There is also disclosed a safety indwelling needle in which a spring-type needlepoint protecting means is disposed within an outer needle hub, and when an inner needle is drawn out, the needlepoint protecting means comes apart from the outer needle hub and covers a distal end of the inner needle (for example, Japanese Patent Laid-Open No. 102345/2002).

Furthermore, there is disclosed a safety indwelling needle in which a sliding cover provided on an inner needle is extended when the inner needle is drawn out from an outer needle so that the entire needle is stored within the cover (for example, Japanese Patent No. 3400550 and Japanese Patent Laid-Open No. 148270/1995).

In the safety indwelling needles provided with a safety mechanism in the related art, since the needlepoint protecting means for covering the inner needle drawn out from an outer needle unit is required to store the entire inner needle, the size of the indwelling needle itself is significant. Also, the safety indwelling needle provided with a spring as the needlepoint protecting means had a problem in that friction between the inner needle and the needlepoint protecting means is large by an urging force of the spring and a drawing-out resistance of the inner needle is also large. Therefore, a force required for drawing out the inner needle is increased and the usableness of the indwelling needle is deteriorated. Furthermore, even when the inner needle is protected by the needlepoint protecting member or the like, there is still a risk of re-projection of the needlepoint from the needlepoint protecting means.

SUMMARY OF THE INVENTION

In view of such circumstances, it is an object of the present invention to provide a safety indwelling needle used for fluid infusion, hemodialysis or the like, which is compact and has a greater usableness and is provided with means for preventing accidental puncture.

In other words, the present invention provides a safety indwelling needle including an inner needle unit having an inner needle, an inner needle hub provided at a proximal end of the inner needle and a housing member disposed at a distal side of the inner needle hub, and an outer needle unit having an outer needle, an outer needle hub provided at a proximal end of the outer needle and an outer needle cap provided on a proximal side of the outer needle hub, characterized in that the housing member includes openings for allowing penetration of the inner needle at a distal end and a proximal end thereof, an internal space for storing only a distal end portion of the inner needle including a needlepoint thereof when the inner needle is drawn out from a state in which the inner needle is inserted into the outer needle, and a shielding member which automatically closes the opening at the proximal end of the housing member by a magnetic force, and the inner needle unit further includes a drop-out preventing means on a surface of the inner needle for preventing the housing member from separating from the inner needle unit.

A safety indwelling needle according to the present invention is adapted to store at least a distal end portion of a pointed inner needle within a housing member by drawing out an inner needle unit. According to the present invention, it is possible to provide a safety indwelling needle having minimum possibility of re-projection of the distal end of the inner needle from the housing member by closing an opening provided on a distal end of the housing member after the inner needle is stored. It is also possible to provide a safety indwelling needle having a satisfactory usableness without increasing drawing-out resistance of the inner needle while drawing out.

Additionally, in the safety indwelling needle of the present invention, since a housing member is connected to an outer needle cap by a suitable force, the housing member can come apart from the outer needle cap and store the distal end of the inner needle in a process that the inner needle unit is pulled out from the outer needle unit. Therefore, it is possible to easily prevent accidental puncture without an additional process for storing the distal end of the inner needle.

DESCRIPTION OF THE DRAWINGS

The safety indwelling needle of the present invention is described in detail below by referring to preferable embodiments shown in the appended drawings. However, the present invention is not limited to these embodiments.

Within the description of the embodiments, a side toward medical personnel during use is referred to as a proximal side, and a side toward a patient is referred to as a distal side. Also, especially in an explanation of an end portion of structural elements, an end of an element on the side of the medical personnel is referred to as a proximal end and an end of the element on the side of the patient is referred to as a distal end.

DETAILED DESCRIPTION OF THE INVENTION

The safety indwelling needle according to an embodiment of the present invention as shown in FIGS. 1 to 5 is used as an indwelling needle especially suitable for blood purification such as artificial dialysis.

Figure 1:
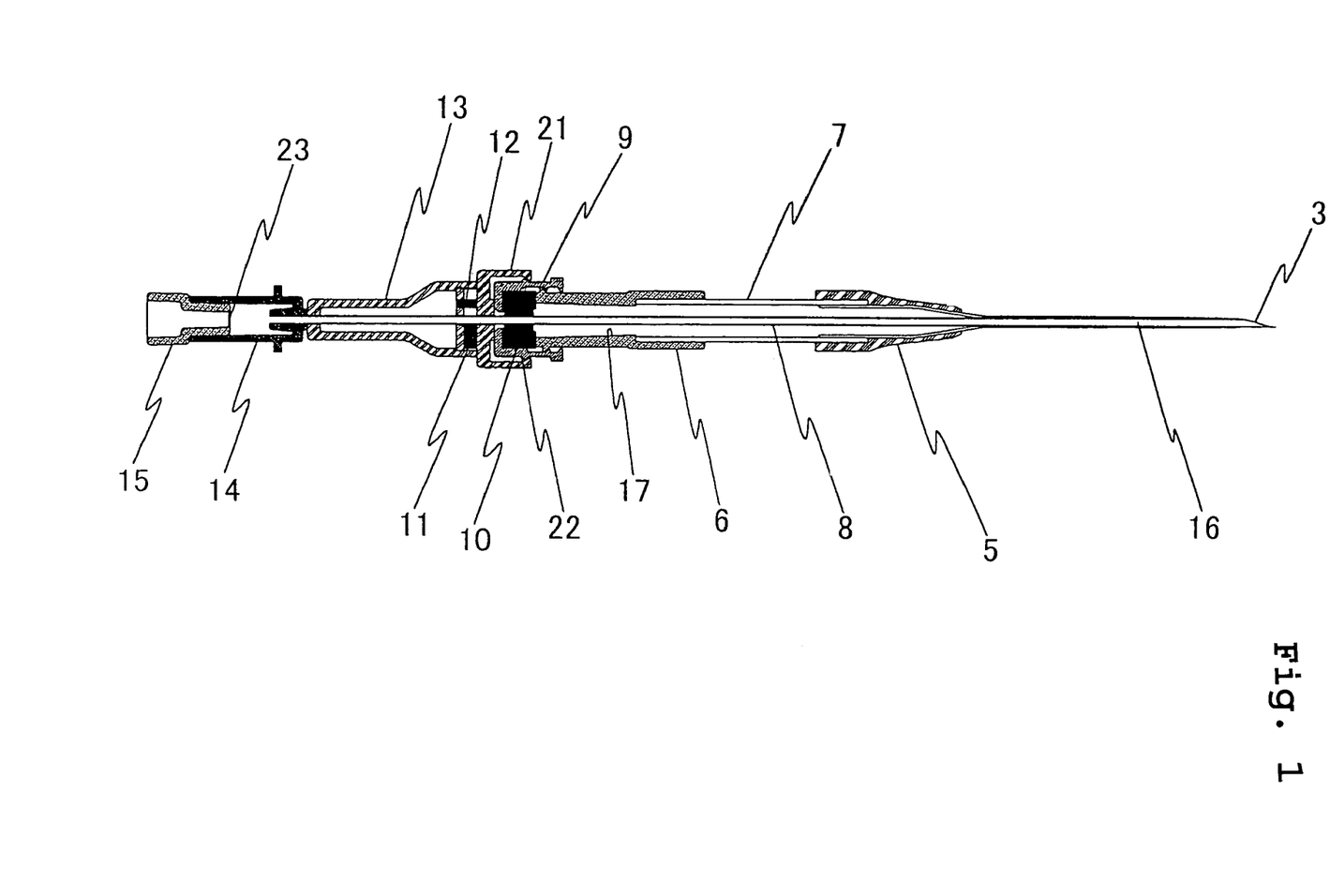
FIG. 1 is a cross-sectional view of the safety indwelling needle according to an embodiment of the present invention before use.
Figure 2:
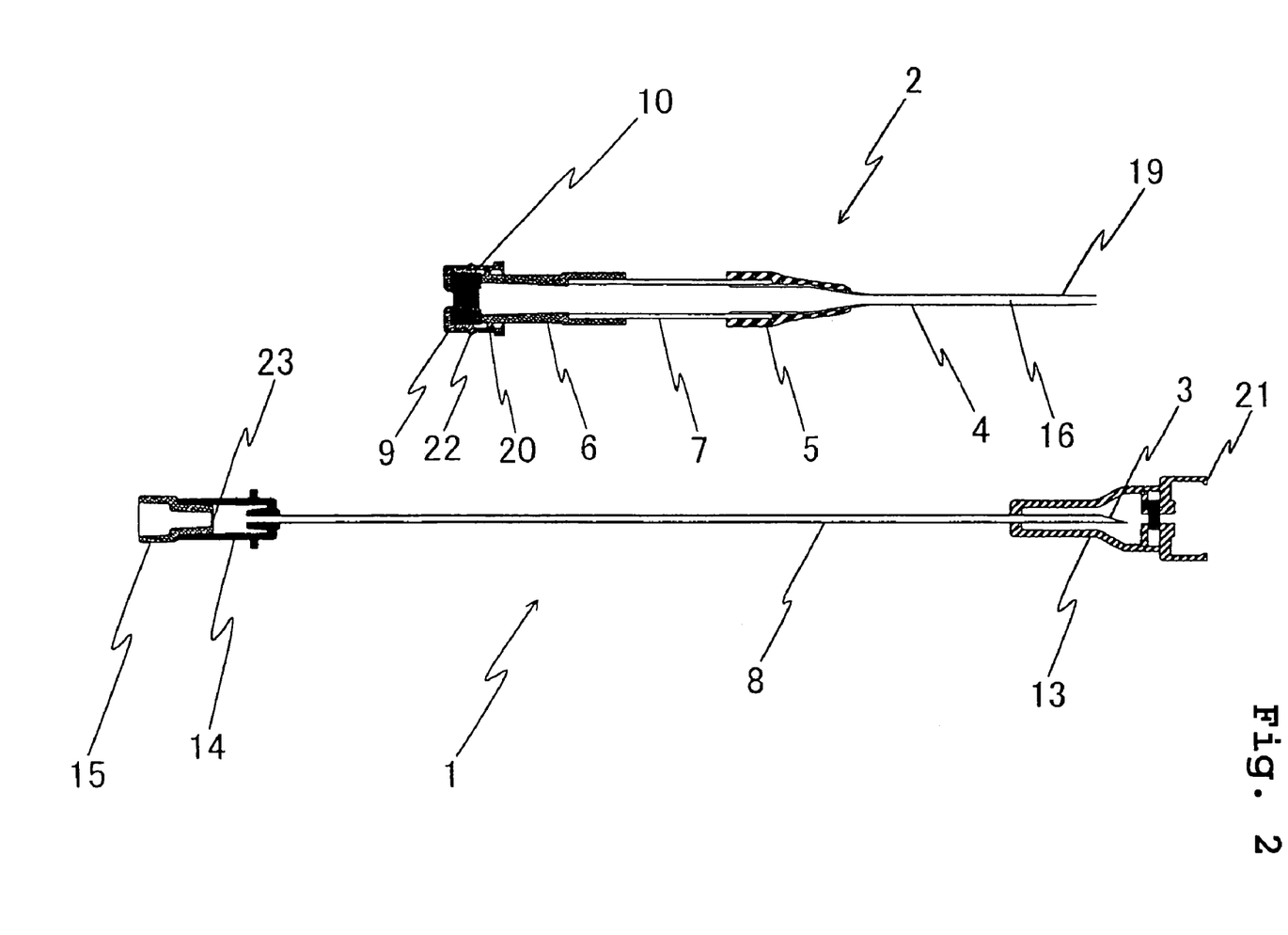
FIG. 2 is a cross-sectional view of the safety indwelling needle shown in FIG. 1 after pulling out an inner needle unit.

The safety indwelling needle shown in FIG. 1 and FIG. 2 comprises an inner needle unit 1 and an outer needle unit 2. The inner needle unit 1 includes an inner needle 8 having a pointed needlepoint 3 at a distal end thereof and an inner needle hub 14 at a proximal end thereof, an inner needle cap 15 mounted on the inner needle hub 14, and a housing member 13 for storing and covering the pointed needlepoint 3 of the inner needle 8 after the inner needle 8 of the inner needle unit 1 is drawn out from the outer needle unit 2.

The outer needle unit 2 includes an outer needle 4 having a lumen 16 in which the inner needle B of the inner needle unit 1 is inserted at a proximal side of the outer needle unit 2, an outer needle hub 5 and an outer needle connector 6 at a proximal side of the outer needle unit 2, a flexible tube 7 for connecting the outer needle hub 5 and the outer needle connector 6, and an outer needle cap 9.

The outer needle 4 of the outer needle unit 2 preferably has a hollow shape and suitable flexibility. The preferable material for the outer needle 4 is a soft resin, such as ethylene-tetrafluoroethylene copolymer (ETFE), polyurethane, a polyether-nylon resin, polypropylene or the like. The outer needle 4 may partly or entirely provide visibility of the interior. It is also possible to blend X-ray contrast mediums, such as barium sulfate or barium carbonate, in the material for the outer needle 4 to provide a radiographic function.

The portion in the vicinity of a distal end of the outer needle 4 is preferably tapered so that an outer diameter of the outer needle 4 is gradually reduced toward the distal end in order to easily perform puncture into the skin of a living body with a less invasive manner. It is also possible to provide one or a plurality of holes 19 in the vicinity of the distal end of the outer needle 4 in order to allow liquid flowing in the outer needle 4 to efficiently come in and out. The outer needle hub 5 is secured to a proximal end of the outer needle 4 in a liquid-tight manner, and the lumen 16 of the outer needle 4 and an interior of the outer needle hub 5 communicate with each other. The tube 7 is connected to the outer needle hub 5 and is further provided with the outer needle connector 6 having a female luer taper 17 therein to be connected to a separate medical instrument. It is possible to provide the connector 6 with a locking means 20 on an outer periphery thereof in the vicinity of the proximal end in order to ensure connection with the separate medical instrument. The outer needle unit 2 may be connected to the separate medical instrument by utilizing flexibility of the tube 7 without providing the unit with the outer needle connector 6.

The outer needle cap 9 is fitted on the outer needle connector 6. The outer needle cap 9 is provided therein with a packing 10 having resiliency through which the inner needle can pass. After the inner needle 1 is drawn out from the outer needle unit 2, the packing 10 closes a through hole which is made by the inner needle 1 and prevents fluid from flowing out from the proximal end of the outer needle unit 2.

Figure 3:
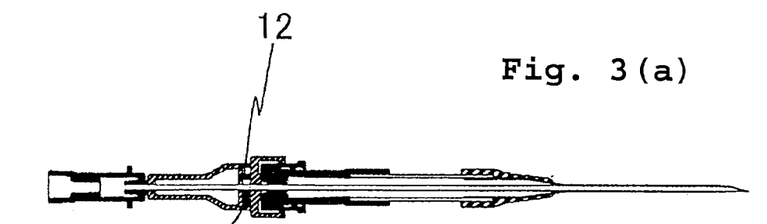
FIG. 3 is an illustration showing a process for using the safety indwelling needle shown in FIG. 1 and FIG. 2.

The housing member 13 for storing and covering the needlepoint 3 of the inner needle 8 provided on the inner needle unit 1 is detachably connected to the outer needle cap 9. The means of connecting the outer needle cap 9 and the housing member 13 is not specifically limited. However, it is preferable that the housing member 13 is fixed to the outer needle cap 9 in a process of drawing the inner needle unit 1 out from the outer needle unit 2, and when a projecting portion 18 as a drop-out preventing means provided on the inner needle 8 (see FIG. 5) reaches an inner wall at the proximal end of the housing member 13 shown in FIG. 3(C), the housing member 13 comes away from the outer needle cap 9 by further drawing the inner needle unit 1. For example, it is achieved by providing the housing member 13 and the outer needle cap 9, respectively, with a flexible hook-shaped member 21 and a projecting portion 22 which is engaged by the hook-shaped member 21 so that the outer needle cap 9 is detachably fixed to the housing member 13 by engagement of the hook-shaped member 21 and the projecting portion 22. The hook-shaped member 21 or the projecting portion 22 may be provided on any one of the outer needle cap 9 and the housing member 13 as long as the outer needle cap 9 is detachably fixed to the housing member 13.

The inner needle 8 is a hollow needle, and materials such as stainless steel, aluminum, aluminum alloy, titanium or titanium alloy may be employed as a material of the inner needle 8. In view of processability and cost, stainless steel is preferably used for the inner needle 8. The pointed needlepoint 3 is formed at the distal end of the inner needle 8. The shape of the needlepoint 3 is not specifically limited. In this embodiment, the needlepoint 3 has an edge surface which is inclined by a predetermined angle with respect to an axis of the inner needle 8.

Figure 5:
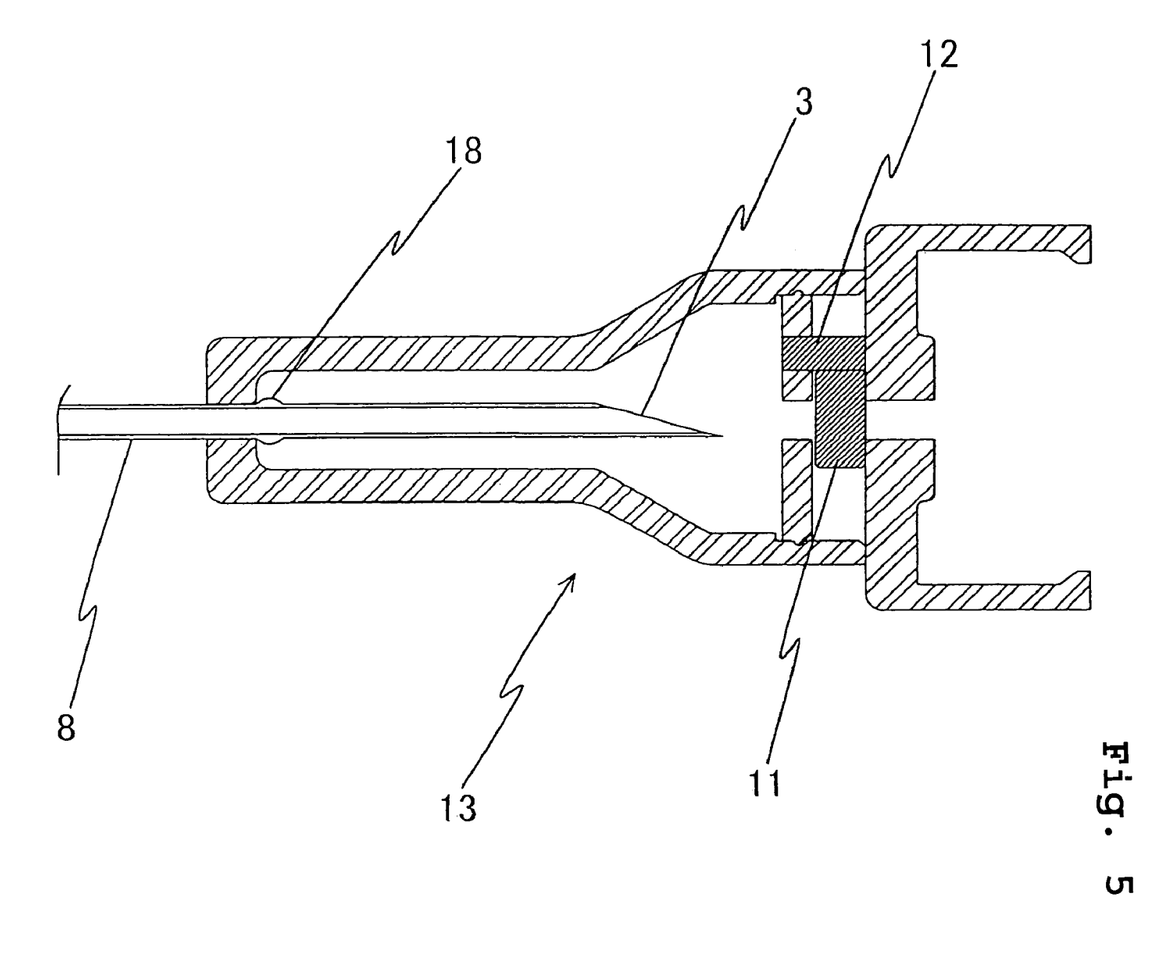
FIG. 5 is an enlarged cross-sectional view of a housing member of the safety indwelling needle shown in FIG. 1.

As shown in FIG. 5, the drop-out preventing means intended for preventing the housing member 13 from dropping out, or separating, from the inner needle unit 1 is provided on a part of the surface of the inner needle 8. The drop-out preventing means may be an irregular portion provided on the inner needle 8, which is, for example, a projection 18 provided on the circumferential surface of the inner needle 8. The projection 18 may be a doughnut-shaped projection extending along the entire circumference of the inner needle 8 or one or more projections which are partly provided on the circumference of the inner needle 8. The position where the projection 18 is provided may be, as shown in FIG. 5, the position at which the distal end portion of the inner needle 8 including the needlepoint 3 is completely stored within the housing member 13 in a state in which the projection 18 reaches the inner surface of the proximal side of the internal space of the housing member 13.

As shown in FIG. 1, the inner needle unit 1 is inserted into a lumen of the outer needle unit 2, the housing member 13 through the interior of which the inner needle 8 passes is interposed between a distal end of the inner needle hub 14 and a proximal end of the outer needle cap 9, and is detachably connected to the proximal end of the outer needle cap 9. The proximal end of the inner needle 8 is fixed to the distal end of the inner needle hub 14 in a liquid-tight manner, and a lumen of the inner needle 8 communicates with an internal space of the inner needle hub 14. The inner needle hub 14 is composed of a substantially cylindrical hollow member and fixed to the inner needle 8 by fitting, caulking, fusion bonding, adhesion with an adhesive agent or the like, or a combination of these means. Further, the inner needle hub 14 is preferably transparent, colored transparent, or translucent so that the interior of the inner needle hub 14 is visible for observing flashback of blood.

The inner needle hub 14 is preferably provided at a proximal end thereof with a ventilation filter 23 which can transmit air but block liquid. Alternatively, as shown in FIG. 1, the cap 15 provided with the ventilation filter 23 may be attached to the proximal end of the inner needle hub 14. As the ventilation filter 23, for example, various sintered porous members or hydrophobic non-woven fabrics, or other porous members may be employed. The sintered porous member is preferably formed by sintering a powdered polymer material such as polyethylene and a material containing hydrophilic, water-soluble or water-swelling polymer. By utilizing such a sintered porous member for the ventilation filter 23, the ventilation filter 23 can also block air by contacting with liquid such as blood, and hence invasion of air from the outside can be prevented.

As shown in FIG. 5, the housing member 13 for covering the pointed needlepoint 3 of the inner needle 8 of the inner needle unit 1 after use is formed of a substantially cylindrical member. The housing member 13 includes a main body having an internal space, which can store only the distal end portion of the inner needle 8 including the needlepoint 3, and a shielding member for preventing re-projection of the needlepoint 3 of the inner needle 8 after it is stored in the internal space. The housing member 13 is provided with openings through which the inner needle penetrates at the proximal end and the distal end thereof.

The shape of the openings of the housing member 13 is not limited, but is preferably a substantially circular shape. The opening at the distal end of the housing member 13 has a sufficient size to allow the inner needle 8 and the projection 18 as the drop-out preventing means formed on the surface of the inner needle 8 to pass through, and a shape to be closed by a first shielding member 11 after the inner needle unit 1 is drawn out. The opening at the proximal end of the housing member 13 is also preferably a substantially circular shape and has a size which does not allow the above-described projection 18 to pass through. Furthermore, the housing member 13 may be provided with a hard O-ring (not shown) formed of a metal or the like and having an inner diameter, which allows the inner needle 8 to pass through, and is equal to an outer diameter of the inner needle 8 and does not allow the projection 18 to pass through. The inner needle 8 is prevented from being drawn out from the housing member 13 further reliably by providing the O-ring. The O-ring is preferably fixed to the proximal end within the housing member 13.

Furthermore, a liquid absorbing member (not shown) for absorbing blood, body fluid or the like may be provided in the internal space of the housing member 13. The material for the liquid absorbing member may be, for example, sponge, polyurethane, a rubbery resilient member or the like.

Figures 4A, 4B:
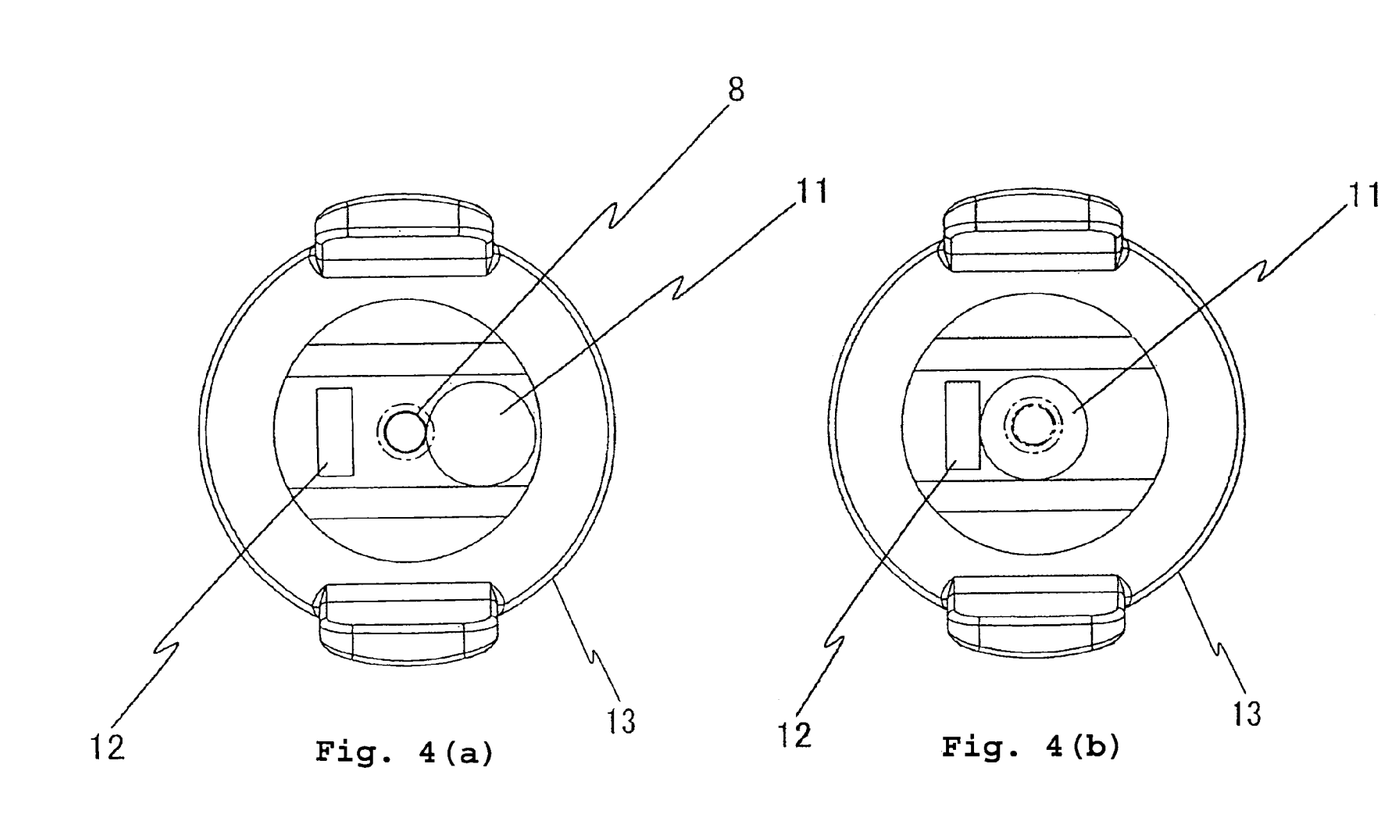
FIG. 4 is an enlarged cross-sectional view of a shielding member of the safety indwelling needle shown in FIG. 1.

Before use, as shown in FIG. 4(A), the inner needle 8 penetrates the housing member 13 and the opening at the distal end of the housing member 13 is opened. After use, as shown in FIG. 4(B), the inner needle 8 is drawn out from the outer needle unit 2, the needlepoint 3 of the inner needle 8 is stored within the housing member 13 and the opening at the distal end of the housing member 13 is closed by the shielding member. The shielding member is preferably formed of a combination of a magnetic substance such as stainless steel and a magnet, or a combination of magnets. The opening at the distal end of the housing member 13 is automatically closed by sliding of the magnet or the magnetic substance.

As shown in FIG. 4, the shielding member includes a first shielding member 11 and a second shielding member 12. In a state in which the inner needle 8 penetrates the housing member 13 as shown in FIG. 4(A), the first shielding member 11 is attracted toward the second shielding member 12 by a magnetic force, but is constrained by the inner needle 8. When the inner needle unit 1 is drawn out from the outer needle unit 2 and the needlepoint 3 of the inner needle 8 is stored within the housing member 13, the constraint of the first shielding member 11 by the inner needle 8 is released. Therefore, the first shielding member 11 is attracted by the second shielding member 12 and slides toward the second shielding member 12 by a magnetic force exerted between the first shielding member 11 and the second shielding member 12. At this time, the opening at the distal end of the housing member 13 is closed by the first shielding member 11, and hence the re-projection of the needlepoint 3 of the inner needle 8 and leakage of blood or the like can be reliably prevented.

The material for the magnet used for the shielding member is not specifically limited, but may be samarium-cobalt magnet, aluminum-nickel-cobalt magnet, neodymium magnet, ferrite magnet or the like. The material of the magnetic substance used for the shielding member is also not specifically limited as long as it is attracted by the magnet, but stainless steel having magnetism is preferable from the point of view that it hardly rusts. The shape of the first shielding member 11 is not specifically limited as long as it can close the opening at the distal end of the housing member 13 after the inner needle 8 is drawn out. The first shielding member 11 preferably has a column shape which has a thickness of about 1 mm and a circular cross section and can close the opening at the distal end of the housing member 13.

The first shielding member 11 may be provided with a conical depressed portion at the proximal end thereof, concretely, at a position that the needlepoint 3 of the inner needle 8 is attached when the needlepoint 3 is stored in the internal space of the housing member 13 and the opening at the distal end of the housing member 13 is closed. When the inner needle 8 is out of the established position within the housing member 13, the depressed portion can prevent the needlepoint 3 from projecting from the opening at the distal end of the housing member 13 with pushing the shielding member 11 which closes the opening or from a position except the opening.

After the safety indwelling needle is punctured into the skin of a body, the inner needle unit 1 is drawn out from the outer needle unit 2 as shown in FIG. 3(B). When the inner needle unit 1 is further drawn out to a state shown in FIG. 3(C), the needlepoint 3 of the inner needle 8 is stored within the housing member 13, and the first shielding member 11 constrained by the inner needle 8 is attracted toward the second shielding member 12 by the magnetic force, whereby the opening at the distal end of the housing member 13 is closed by the first shielding member 11.

When the inner needle unit 1 is further drawn to a state shown in FIG. 3(D), the housing member 13 cannot slide anymore on the inner needle 8 due to the existence of the projection 18 provided on the inner needle 8 of the inner needle unit 1, whereby the housing member 13 comes apart from the outer needle cap 10. Accordingly, the inner needle unit 1 and the outer needle unit 2 are separated and the inner needle unit 1 can be safely disposed.

Subsequently, the safety indwelling needle according to another embodiment of the present invention as shown in FIGS. 6 to 9 is specifically used as an indwelling needle used especially for fluid infusion or the like.

Figure 6:
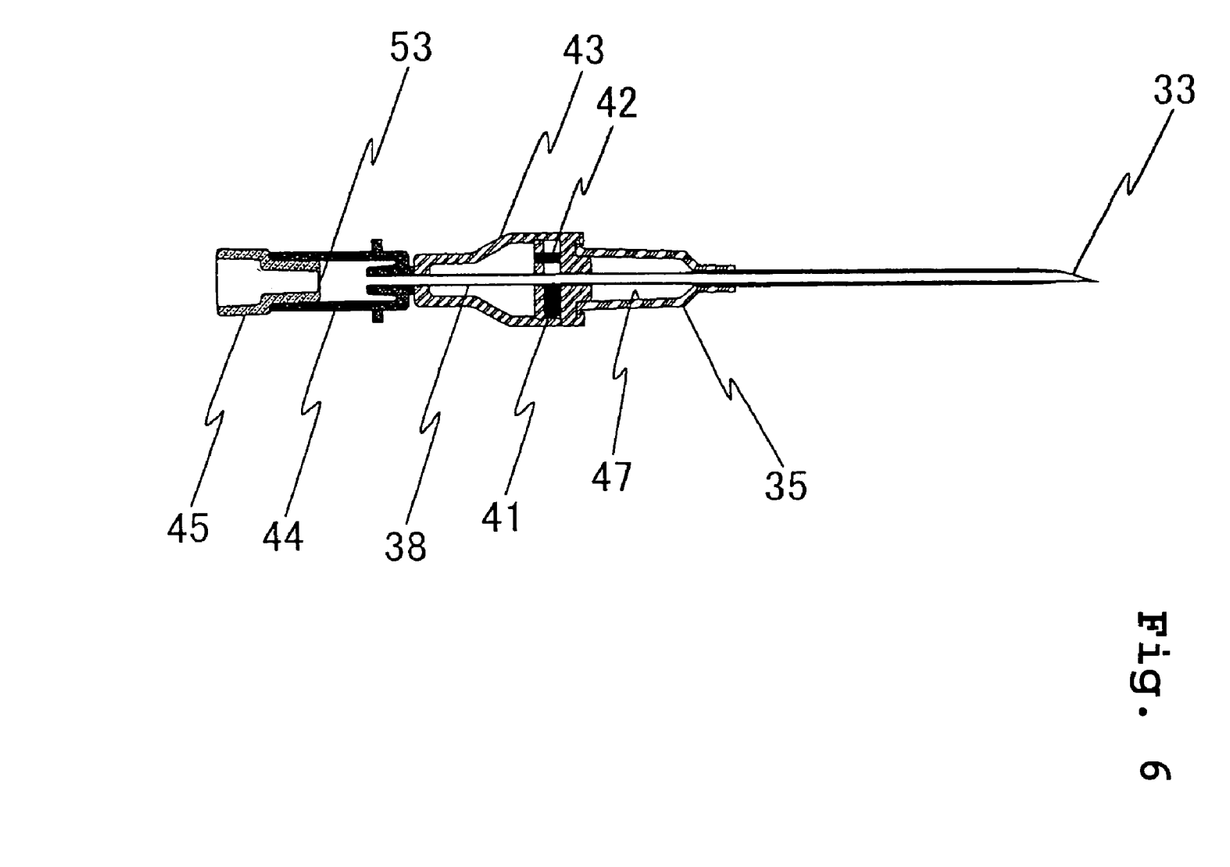
FIG. 6 is a cross-sectional view of the safety indwelling needle according to another embodiment of the present invention before use.
Figure 7:
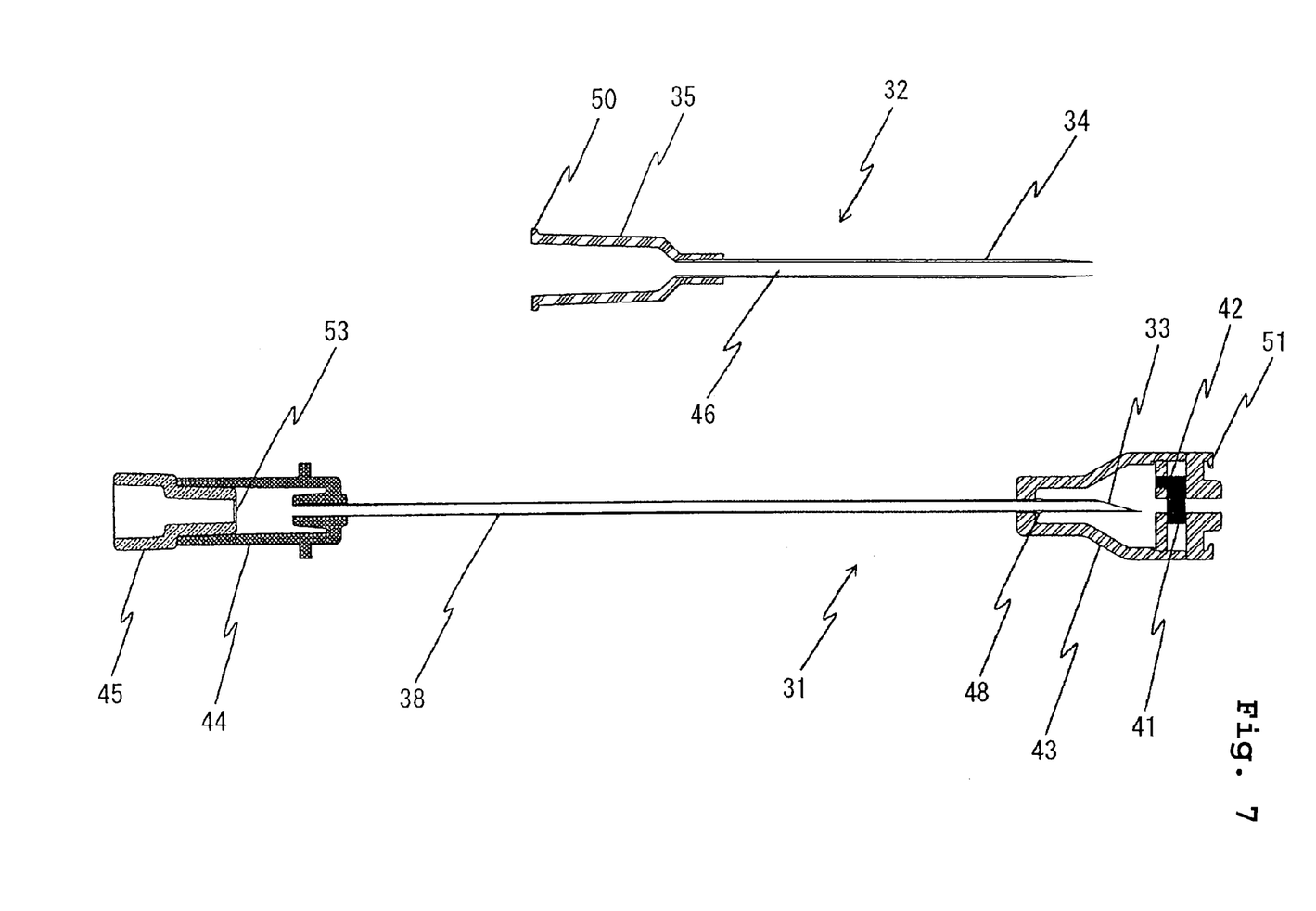
FIG. 7 is a cross-sectional view of the safety indwelling needle shown in FIG. 6 after pulling out an inner needle unit.

The safety indwelling needle shown in FIG. 6 and FIG. 7 comprises an inner needle unit 31 and an outer needle unit 32. The inner needle unit 31 includes an inner needle 38 having a pointed needlepoint 33 at a distal end thereof and an inner needle hub 44 at a proximal end thereof, an inner needle cap 45 fitted on the inner needle hub 44, and a housing member 43 for storing and covering the pointed needlepoint 33 of the inner needle 38 after the inner needle 38 of the inner needle unit 31 is drawn out from the outer needle unit 32.

The outer needle unit 32 includes at a distal side thereof an outer needle 34 having a lumen 46 in which the inner needle 38 of the inner needle unit 31 is inserted, and an outer needle hub 35 at a proximal side of the outer needle unit 32.

The outer needle 34 of the outer needle unit 32 preferably has a hollow shape and suitable flexibility. The preferable material for the outer needle 34 is a soft resin, such as ethylene-tetrafluoroethylene copolymer (ETFE), polyurethane, a polyether-nylon resin, polypropylene or the like. The outer needle 34 may partly or entirely have visibility of the interior. It is also possible to blend X-ray contrast mediums, such as barium sulfate or barium carbonate in the material for the outer needle 34 to provide a radiographic function.

The portion in the vicinity of a distal end of the outer needle 34 is preferably tapered so that an outer diameter of the outer needle 34 is gradually reduced toward the distal end in order to easily perform puncture into a living body with little invasiveness. It is also possible to provide the outer needle 34 with one or a plurality of holes (not shown) in the vicinity of the distal end thereof in order to allow liquid flowing in the outer needle 34 to efficiently come in and out. The outer needle hub 35 is secured to a proximal end of the outer needle 34 in a liquid-tight manner, and the lumen 46 of the outer needle 34 and an interior of the outer needle hub 35 communicate with each other. The configuration of an inner surface of the outer needle hub 35 is preferably formed with a female luer taper 47 to be connected to a medical instrument such as a fluid infusion set or a syringe. It is also possible to provide the outer needle hub 35 with a locking means 50 on an outer periphery of the outer needle hub 35 at a proximal side thereof for ensuring connection with the separate medical instrument.

The housing member 43 for storing and covering the needlepoint 33 of the inner needle 38 provided in the inner needle unit 31 is detachably connected to the outer needle hub 35. The connecting means between the outer needle hub 35 and the housing member 43 is not specifically limited. However, it is preferable that the housing member 43 is fixed to the outer needle hub 35 in a process of drawing the inner needle unit 31 out from the outer needle unit 32, and when a projection 48 as a drop-out preventing means provided on the inner needle 38 reaches an inner wall at the proximal end of the housing member 43 as shown in FIG. 8(C), the housing member 43 comes away from the outer needle hub 35 by further drawing the inner needle unit 31. For example, it is achieved by providing the housing member 43 and the outer needle hub 35 with a hook-shaped member 51 and a projecting portion, respectively, which is engaged by the hook-shaped member 51 so that the outer needle hub 35 is detachably fixed to the housing member 43. As the projecting portion, a locking means 50 provided on the outer needle hub 35 may be used in this embodiment.

The inner needle 38 is a hollow needle, and materials such as stainless steel, aluminum, aluminum alloy, titanium, or titanium alloy may be employed as a material of the inner needle 38. In view of processability and cost, stainless steel is preferably used for the inner needle 38. The pointed needlepoint 33 is formed at the distal end of the inner needle 38. The shape of the needlepoint 33 is not specifically limited. In this embodiment, the needlepoint 33 has an edge surface which is inclined by a predetermined angle with respect to an axis of the inner needle 38.

Figure 9:
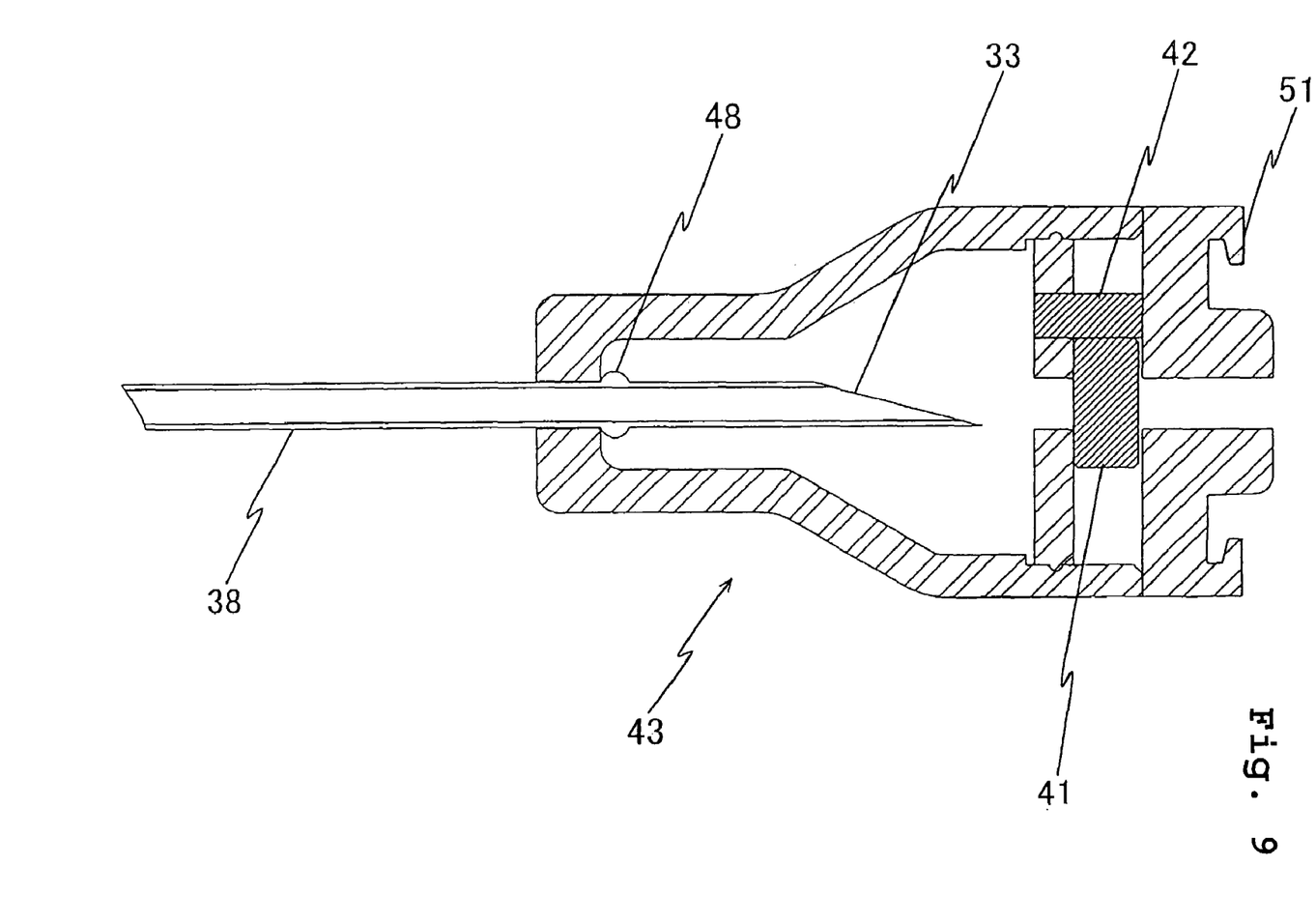
FIG. 9 is an enlarged cross-sectional view of a housing member of the safety indwelling needle shown in FIG. 6.

As shown in FIG. 9, the drop-out preventing means intended for preventing the housing member 43 from dropping out from the inner needle unit 31 is provided on a part of the surface of the inner needle 38. The drop-out preventing means may be an irregular portion on the inner needle 38 which is, for example, the projection 48 provided on the circumferential surface of the inner needle 38. The projection 48 may be a doughnut-shape projection extending along the entire circumference of the inner needle 38 or one or more projections which are partly provided on the circumference of the inner needle 38. When it is formed on part of the circumference, a plurality of projections may be formed on the circumference. The position where the projection 48 is provided may be, as shown in FIG. 9, the position at which the distal end portion of the inner needle 38 including the needlepoint 33 is completely stored within the housing member 43 in a state in which the projection 48 reaches the inner surface of the proximal side of the internal space of the housing member 43.

The inner needle unit 31 is inserted into a cavity of the outer needle unit 32, and the housing member 43 through the interior of which the inner needle 38 passes is interposed between a distal end of the inner needle hub 44 and a proximal end of the outer needle hub 35, and is detachably connected to the proximal end of the outer needle hub 35. The proximal end of the inner needle 38 is connected to the distal end of the inner needle hub 44 in a liquid-tight manner, and a lumen of the inner needle 38 communicates with an internal space of the inner needle hub 44. The inner needle hub 44 is composed of a substantially cylindrical hollow member and is fixed to the inner needle 38 by fitting, caulking, fusion bonding, adhesion with adhesive agent or the like or a combination of these means. Further, the inner needle hub 44 is preferably transparent, colored transparent or translucent so that the interior of the inner needle hub 44 is visible for observing flashback of blood.

The inner needle hub 44 is preferably provided with a ventilation filter 53 which can transmit air but block liquid at a proximal end thereof. Alternatively, as shown in FIG. 6, the cap 45 provided with a ventilation filter 53 may be attached to the proximal end of the inner needle hub 44. As the ventilation filter 53, for example, various sintered porous members or hydrophobic non-woven fabrics, or other porous members may be employed. The sintered porous member is preferably formed by sintering a powdered polymer material such as polyethylene and a material containing hydrophilic, water-soluble, water-swelling polymer. By utilizing such a sintered porous member for the ventilation filter 53, the filter can also block air by contacting with a liquid such as blood, and hence invasion of air from the outside can be prevented.

As shown in FIG. 9, the housing member 43 for covering the pointed needlepoint 33 of the inner needle 38 of the inner needle unit 31 after use is formed of a substantially cylindrical member. The housing member 43 includes a main body having an internal space, which can store only the distal end portion of the inner needle 38 including the needlepoint 33, and a shielding member for preventing re-projection of the needlepoint 33 of the inner needle 38 after being stored in the internal space. The housing member 43 is provided with openings through which the inner needle penetrates at the proximal end and the distal end thereof.

The shape of the openings of the housing member 43 is not limited, but is preferably a substantially circular shape. The opening at the distal end of the housing member 43 has a sufficient size to allow the inner needle 38 and the projection 48, as the drop-out preventing means formed on the surface of the inner needle 38, to pass through, and a shape to be closed by a first shielding member 41 after the inner needle unit 31 is drawn out. The opening at the proximal end of the housing member 43 is also preferably a substantially circular shape and has a size which does not allow the above-described projection 48 to pass through. Furthermore, the housing member 43 may be provided with a hard O-ring (not shown) formed of a metal or the like and having an inner diameter, which allows the inner needle 38 to pass through, is equal to an outer diameter of the inner needle 38, and does not allow the projection 48 to pass through. The inner needle 38 is prevented from being drawn out from the housing member 43 further reliably by providing the O-ring. The O-ring is preferably fixed to the proximal end within the housing member 43.

Furthermore, a liquid absorbing member (not shown) for absorbing blood, body fluid or the like may be provided in the internal space of the housing member 43. The material for the liquid absorbing member may be, for example, sponge, polyurethane, a rubbery resilient member or the like.

The structure of the shielding member provided within the housing member 43 in this embodiment is substantially the same as the structure of the shielding member of the safety indwelling needle shown in FIGS. 1 to 5. The shielding member includes a first shielding member 41 and a second shielding member 42. The shielding member is preferably formed of a combination of a magnetic substance such as stainless steel and a magnet, or a combination of magnets. In a state in which the inner needle 38 penetrates the housing member 43, the first shielding member 41 is attracted toward the second shielding member 42 by a magnetic force, but is constrained by the inner needle 38. When the inner needle unit 31 is drawn out from the outer needle unit 32 and the needlepoint 33 of the inner needle 38 is stored within the housing member 43, the constraint of the first shielding member 41 by the inner needle 38 is released. Therefore, the first shielding member 41 is attracted by the second shielding member 42 and slides toward the second shielding member 42 by a magnetic force exerted between the first shielding member 41 and the second shielding member 42. At this time, the opening at the distal side of the housing member 43 is closed by the first shielding member 41, and hence the re-projection of the needlepoint 33 of the inner needle 38 and leakage of blood or the like can be reliably prevented.

The material for the magnet used for the shielding member is not specifically limited, but may be a samarium-cobalt magnet, aluminum-nickel-cobalt magnet, neodymium magnet, ferrite magnet or the like. The material of the magnetic substance used for the shielding member is also not specifically limited as long as it is attracted by the magnet, but stainless steel having magnetism is preferable from the point of view that it hardly rusts. The shape of the first shielding member 41 is not specifically limited as long as it can close the opening at the distal end of the housing member 43 after the inner needle 38 is drawn out. The first shielding member 41 preferably has a columnar shape which has a thickness of about 1 mm and a circular cross section and can close the opening at the distal end of the housing member 43.

The first shielding member 41 may be provided with a conical depressed portion at the proximal end thereof, concretely, at a position that the needlepoint 33 of the inner needle 38 is attached when the needlepoint 33 is stored in the internal space of the housing member 43 and the opening at the distal end of the housing member 43 is closed. When the inner needle 38 is out of the established position within the housing member 43, the depressed portion can prevent the needlepoint 33 from projecting from the opening at the distal end of the housing member 43 with pushing the shielding member 41 which closes the opening or from a position except the opening.

Figures 8A, 8B:
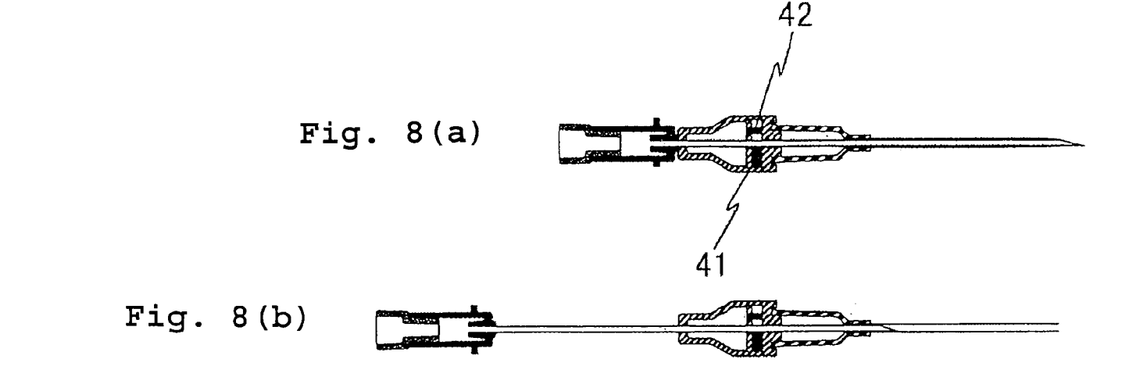
FIG. 8 is an illustration showing a process for using the safety indwelling needle shown in FIG. 6 and FIG. 7.
Figures 8C, 8D:
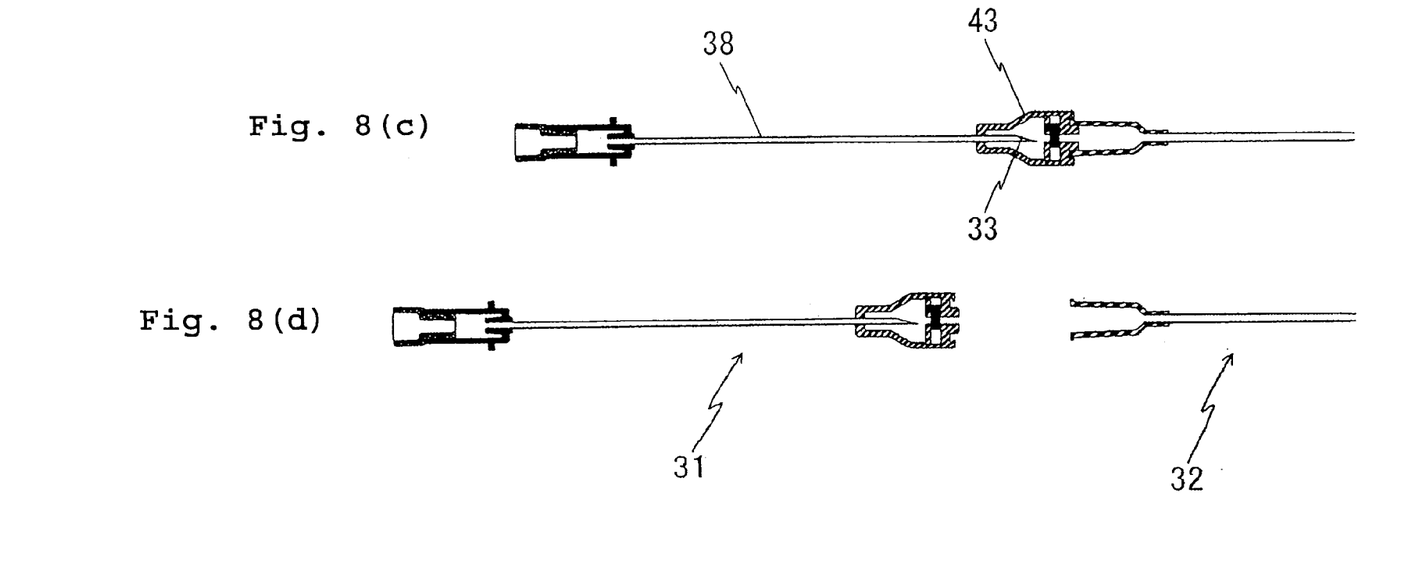

After the safety indwelling needle is punctured into the skin of a body, the inner needle unit 31 is drawn out from the outer needle unit 32 as shown in FIG. 8(B). When the inner needle unit 31 is further drawn out to a state shown in FIG. 8(C), the needlepoint 33 of the inner needle 38 is stored within the housing member 43, and the first shielding member 41 constrained by the inner needle 38 is attracted toward the second shielding member 42 by the magnetic force, whereby the opening at the distal end of the housing member 43 is closed by the first shielding member 41.

When the inner needle unit 32 is further drawn to a state shown in FIG. 8(D), the housing member 43 cannot slide anymore on the inner needle 38 due to existence of the projection 48 provided on the inner needle 38 of the inner needle unit 31, whereby the housing member 43 comes apart, i.e., separates, from the outer needle hub 35. Accordingly, the inner needle unit 31 and the outer needle unit 32 are separated and the inner needle unit 31 can be safely disposed.

Subsequently, the safety indwelling needle according to still another embodiments of the present invention is shown in FIGS. 10 to 13. In FIGS. 10 to 13, structural elements of the safety indwelling needles of these embodiments, which are the same as structural elements of the safety indwelling needle of the embodiment shown in FIG. 1, are respectively identified using the same reference numbers as in FIG. 1.

Figure 10:
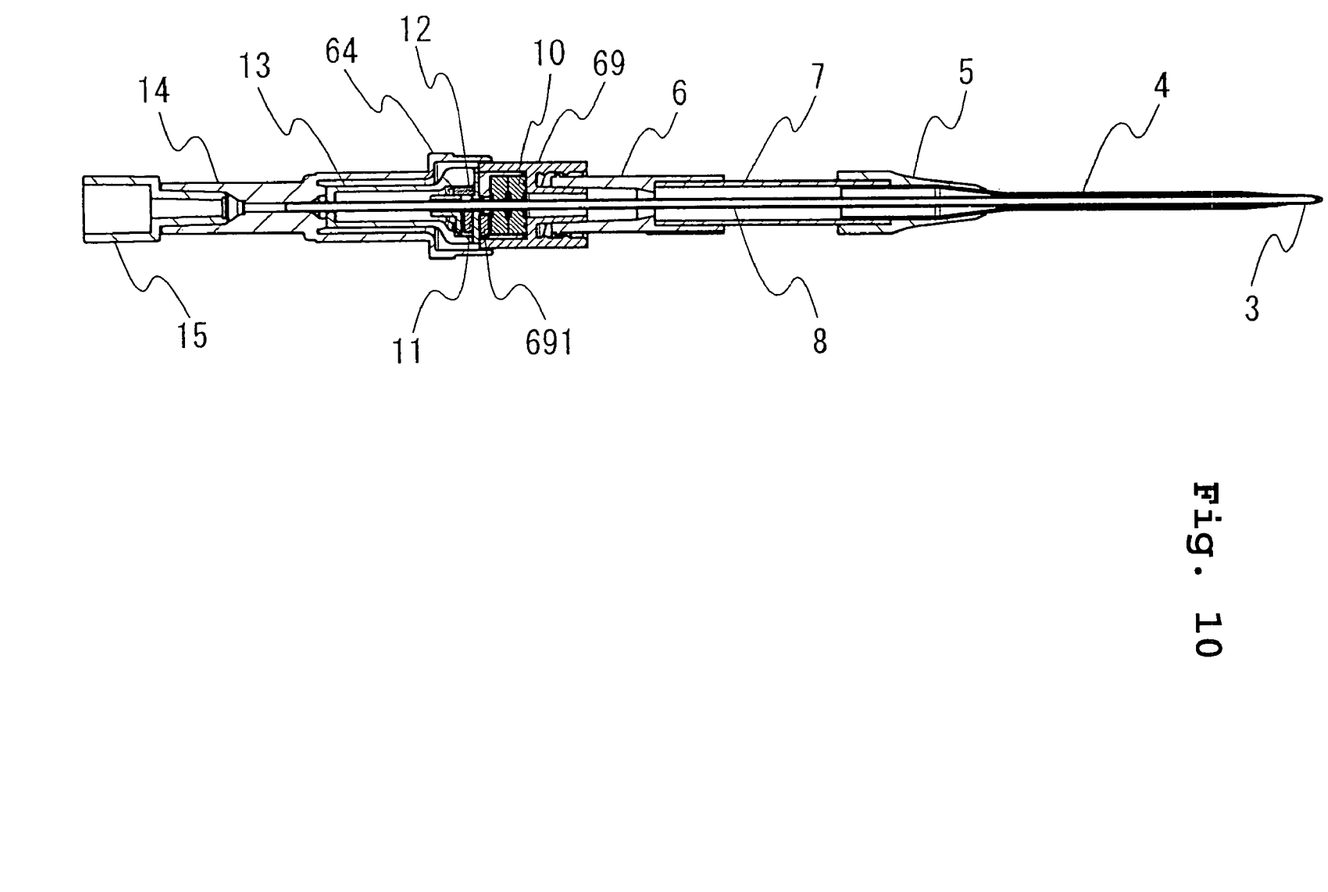
FIG. 10 is a cross-sectional view of the safety indwelling needle according to still another embodiment of the present invention.
Figure 11:
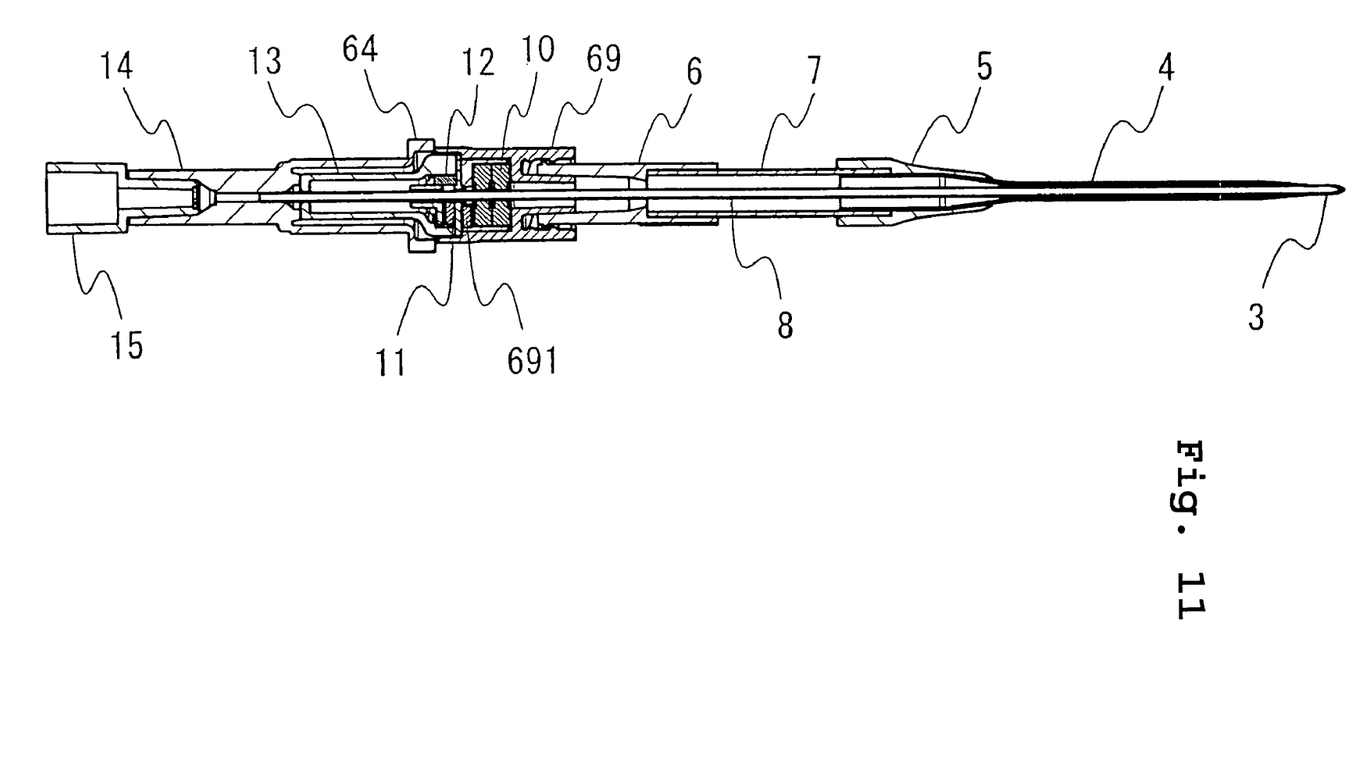
FIG. 11 is a cross-sectional view of the safety indwelling needle according to still another embodiment of the present invention.

The safety indwelling needles shown in FIGS. 10 and 11 are provided in the interior at the distal end of an outer needle cap 69 with a magnet or a magnetic substance 691. The housing member 13 is detachably connected to the outer needle cap 69 by a magnetic force exerted between the magnet or the magnetic substance 691 and the shielding member provided on the housing member 13. As a material of the magnet or the magnetic substance 691, the same material as the material for the magnet or the magnetic substance used for the shielding member provided in the housing member 13 can be used.

The magnetic force exerted between the magnet or the magnetic substance 691 and the shielding member is preferably large enough to fix the housing member 13 to the outer needle cap 69 in a process of drawing the inner needle unit 1 out from the outer needle unit 2, and for the housing member 13 to separate from the outer needle cap 69 by further drawing the inner needle unit 1 when the projection 18 provided on the inner needle 8 reaches the inner wall at the proximal end of the housing member 13 as shown in FIG. 3(C).

The magnetic force is adjusted in proportion to the shapes of the inner needle unit 1 and the outer needle unit 2 by choosing the material or the size of the magnet or the magnetic substance 691. In a case that the magnet or the magnetic substance 691 is disposed in the outer needle cap 69 apart from the distal end thereof or a case that the shielding member is disposed in the housing member 13 apart from the proximal end thereof, the magnetic force is large enough to be exerted through a part of the outer needle cap 69 and/or a part of the housing member 13.

The magnet or the magnetic substance 691 may be provided in the outer needle cap 69 so that the magnetic force is exerted between the magnet or the magnetic substance 691 and any one of the first shielding member 11 and the second shielding member 12 or between the magnet or the magnetic substance 691 and both of the first shielding member 11 and the second shielding member 12.

In the case that the magnetic force is exerted between the magnet or the magnetic substance 691 and any one of the first shielding member 11 and the second shielding member 12, the magnet or the magnetic substance 691 provided in the outer needle cap 69 is chosen in relation to the material of the first shielding member 11 or the second shielding member 12. That is, in a case that the shielding member is a magnet, the outer needle cap 69 may be provided with the magnet or the magnetic substance 691. On the other hand, in a case that the shielding member is a magnetic substance, the outer needle cap 69 is provided with the magnet 691.

Additionally, in the case that the magnetic force is exerted between the magnet or the magnetic substance 691 and the first shielding member 11 which can slide so as to close the opening at the distal end of the housing member 13, the magnetic force quickly decreases due to sliding of the first shielding member 11 when the needlepoint 3 of the inner needle 8 is stored in the internal space of the housing member 13. Therefore, the housing member 13 quickly separates from the outer needle cap 69.

As shown in FIG. 10, the safety indwelling needle of the present invention may have a housing member 13 which is stored in an inner needle hub 64 in a state that the inner needle 8 penetrates the outer needle 4. There is little concern that with such a safety indwelling needle the housing member 13 will come apart from the outer needle cap 69 when an unexpected force is exerted on the housing member 13. Also as shown in FIG. 11, the safety indwelling needle of which the housing member 13 is stored in both of the inner needle hub 64 and the outer needle cap 69 has the same effects as that of the safety indwelling needle shown in FIG. 10.

Figure 12:
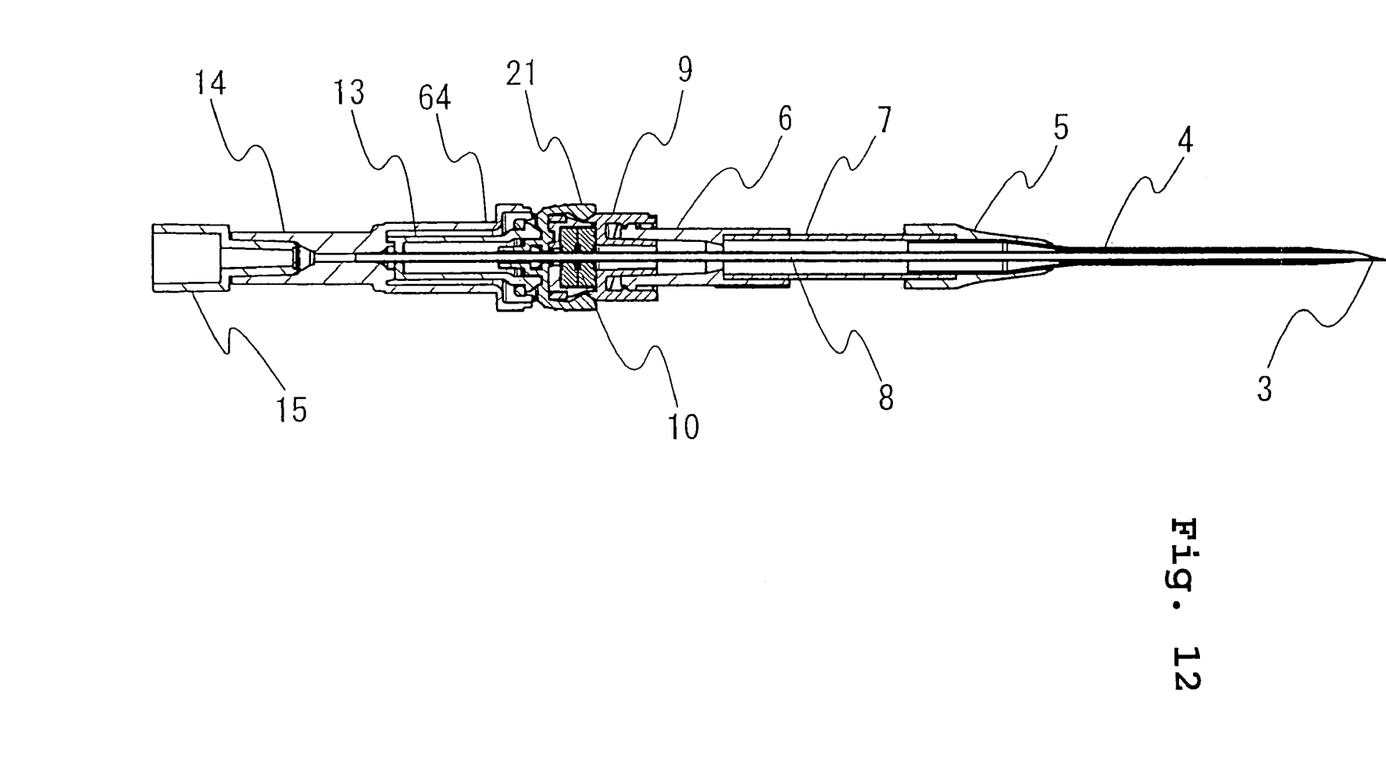
FIG. 12 is a cross-sectional view of the safety indwelling needle according to still another embodiment of the present invention.
Figure 13:
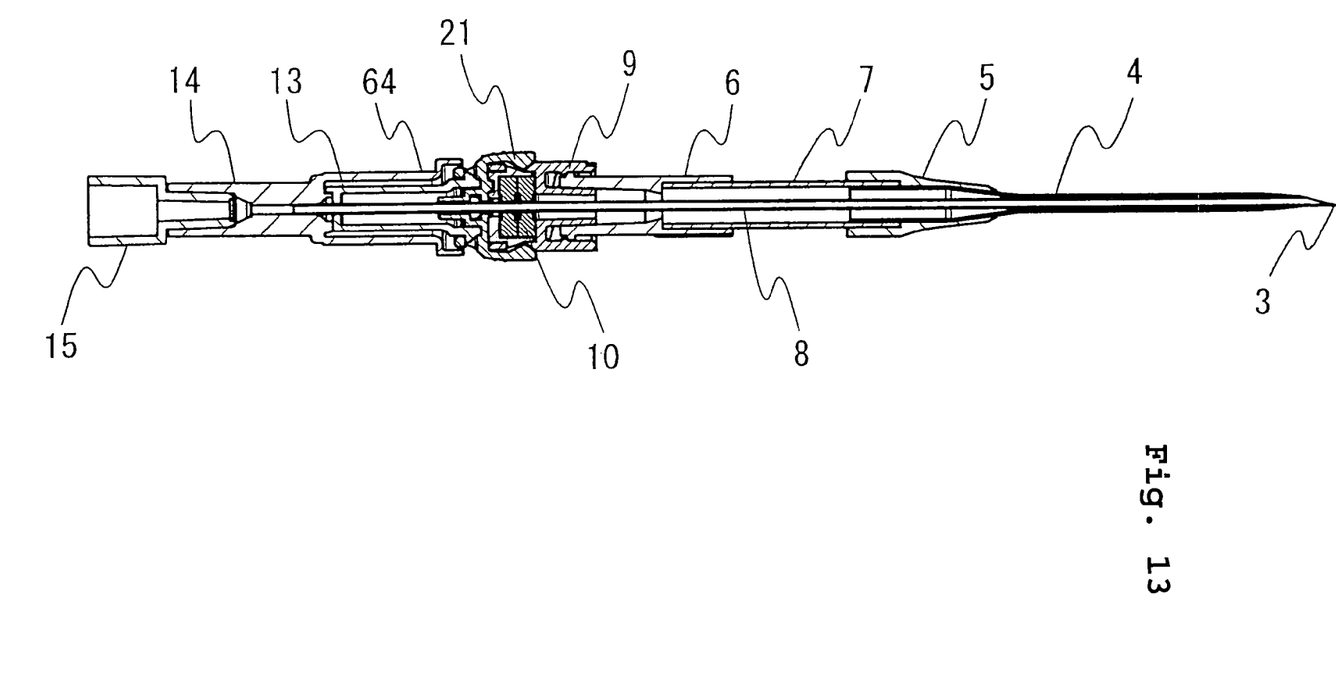
FIG. 13 is a cross-sectional view of the safety indwelling needle according to still another embodiment of the present invention.

In the case that the housing member 13 and the outer needle cap 9 are connected by the hook-shaped member 21 provided on the housing member 13 and the projecting member 22 provided on the outer needle cap 9, the housing member 13 is not entirely stored as shown in FIGS. 10 and 11. The portion of the housing member 13 other than the hook-shaped member 21 may be stored in the inner needle hub 64 as shown in FIG. 12 or in both of the inner needle hub 64 and the outer needle cap 69 as shown in FIG. 13. The safety indwelling needle having such a configuration can prevent the housing member 13 from separating and minimize the outer diameter of the inner needle hub 64 though the hook-shaped member 21 has a large diameter.

The present application claims priority of Japanese application No. 2004-51027, the disclosure of which is incorporated herein by reference.

What is claimed is:

1. A safety indwelling needle including an inner needle unit having an inner needle, an inner needle hub provided at a proximal end of the inner needle and a housing member disposed at a distal side of the inner needle hub, and an outer needle unit comprising an outer needle having a lumen through which the inner needle is inserted, an outer needle hub provided at a proximal end of the outer needle, an outer needle connector provided at the proximal side of the outer needle hub, a tube for connecting a proximal end of the outer needle hub to the distal end of and the outer needle connector and an outer needle cap provided at the proximal end of the outer needle connector for detachably connecting to the housing member, characterized in that the housing member includes openings at a distal end and a proximal end thereof for allowing penetration of the inner needle, an internal space for storing only a distal end portion of the inner needle including a needlepoint thereof when the inner needle is drawn into the housing member from a state in which the inner needle is positioned in the outer needle, and a shielding member which automatically closes the opening at the distal end of the housing member by a magnetic force, and the inner needle unit further includes a drop-out preventing means on a surface of the inner needle for preventing the housing member from separating from the inner needle unit, and wherein the housing member is provided with a hook-shaped member, the outer needle cap is provided with a projecting portion and the housing member is detachably connected to the outer needle cap by engagement between the hook-shaped member and the projecting portion.

2. A safety indwelling needle according to claim 1, wherein the shielding member is formed of a combination of a magnetic substance and a magnet or a combination of magnets, and the opening at the distal end of the housing member is automatically closed by sliding of the magnet or the magnetic substance.

3. A safety indwelling needle according to claim 1, wherein the outer needle cap is provided with a magnet or a magnetic substance, and the housing member is detachably connected to the outer needle cap by a magnetic force exerted between the magnet or the magnetic substance and the shielding member.

4. A safety indwelling needle according to claim 1, wherein the housing member is stored in the inner needle hub in a state that the inner needle penetrates the outer needle.

5. A safety indwelling needle according to claim 1, wherein the housing member is stored in both of the inner needle hub and the outer needle cap in a state that the inner needle penetrates the outer needle.

6. A safety indwelling needle according so claim 1, wherein a portion of the housing member other than the hook-shaped member is stored in the inner needle hub in a state that the inner needle penetrates the outer needle.

7. A safety indwelling needle according to claim 1, wherein a portion of the housing member except the hook-shaped member is stored in both of the inner needle hub and the outer needle cap in a state that the inner needle penetrates the outer needle.

8. A safety indwelling needle according to claim 1, wherein a liquid absorbing member is provided in the internal space of the housing member.

* * * * *